United States Patent
Sato

(10) Patent No.: US 10,142,529 B2
(45) Date of Patent: Nov. 27, 2018

(54) IMAGING APPARATUS AND METHOD FOR MANUFACTURING IMAGING APPARATUS

(71) Applicant: HAMAMATSU PHOTONICS K.K., Hamamatsu-shi, Shizuoka (JP)

(72) Inventor: Takayuki Sato, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 68 days.

(21) Appl. No.: 14/903,474

(22) PCT Filed: Jul. 12, 2013

(86) PCT No.: PCT/JP2013/069202
§ 371 (c)(1),
(2) Date: Jan. 7, 2016

(87) PCT Pub. No.: WO2015/004810
PCT Pub. Date: Jan. 15, 2015

(65) Prior Publication Data
US 2016/0156820 A1   Jun. 2, 2016

(51) Int. Cl.
*H04N 5/225* (2006.01)
*H04N 5/33* (2006.01)
(Continued)

(52) U.S. Cl.
CPC ......... *H04N 5/2256* (2013.01); *G01N 21/645* (2013.01); *G01N 21/6456* (2013.01);
(Continued)

(58) Field of Classification Search
CPC .. G01N 21/645; G01N 21/6456; G01N 21/01; H04N 5/2256; H04N 5/2253; H04N 5/33; G03B 15/02; F21K 9/65
(Continued)

(56) References Cited

U.S. PATENT DOCUMENTS

| | | | |
|---|---|---|---|
| 2002/0001193 A1 | 1/2002 | Osawa et al. | |
| 2007/0053185 A1* | 3/2007 | Whitehead | F21K 9/65 362/249.16 |

(Continued)

FOREIGN PATENT DOCUMENTS

| | | |
|---|---|---|
| DE | 20110289 | 8/2001 |
| EP | 1 762 183 | 3/2007 |

(Continued)

OTHER PUBLICATIONS

International Preliminary Report on Patentability dated Jan. 21, 2016 for PCT/JP2013/069202.

*Primary Examiner* — Andy Rao
*Assistant Examiner* — Zaihan Jiang
(74) *Attorney, Agent, or Firm* — Drinker Biddle & Reath LLP

(57) ABSTRACT

In an imaging device, a tilted surface is formed on one surface side of a base, while a flexible substrate arranged with light sources is secured along the tilted surface of the base, so as to adjust the optical axis of an imaging unit and positions illuminated by the light sources. Thus, the respective optical axes of light sources are regulated not individually but at once by placing the substrate along the tilted surface, which makes it easy to adjust the illumination positions. It is also excellent in heat dissipation of the light sources, since the heat generated by the light sources dissipates through the base. This enables the light sources to keep their output stability favorably.

11 Claims, 8 Drawing Sheets

(51) Int. Cl.
*G01N 21/64* (2006.01)
*G03B 15/02* (2006.01)
*G01N 21/01* (2006.01)
*F21K 9/65* (2016.01)
*F21Y 107/10* (2016.01)

(52) U.S. Cl.
CPC ........... *G03B 15/02* (2013.01); *H04N 5/2253* (2013.01); *H04N 5/33* (2013.01); *F21K 9/65* (2016.08); *F21Y 2107/10* (2016.08); *G01N 21/01* (2013.01)

(58) Field of Classification Search
USPC .......................................................... 348/77
See application file for complete search history.

(56) References Cited

U.S. PATENT DOCUMENTS

| | | | | |
|---|---|---|---|---|
| 2010/0103661 | A1* | 4/2010 | Chiou | G01N 21/8806 362/231 |
| 2010/0309665 | A1* | 12/2010 | Young | F21V 5/002 362/235 |
| 2013/0016210 | A1* | 1/2013 | Smith | G01N 21/55 348/135 |
| 2013/0039056 | A1* | 2/2013 | Cho | F21V 7/0058 362/235 |
| 2014/0268869 | A1* | 9/2014 | Blessitt | G02B 6/0055 362/607 |

FOREIGN PATENT DOCUMENTS

| | | | |
|---|---|---|---|
| JP | 04241476 | A * | 8/1992 |
| JP | H04-241476 | A | 8/1992 |
| JP | H09-147089 | A | 6/1997 |
| JP | 2634700 | | 7/1997 |
| JP | 2001-153808 | A | 6/2001 |
| JP | 2001-358987 | A | 12/2001 |
| JP | 2003-190103 | A | 7/2003 |
| JP | 2003-243856 | A | 8/2003 |
| JP | 2004-361552 | A | 12/2004 |
| JP | 2006-209035 | A | 8/2006 |
| JP | 2008-078066 | A | 4/2008 |
| JP | 2008-122463 | A | 5/2008 |
| JP | 2008-183394 | A | 8/2008 |
| JP | 2009-300871 | A | 12/2009 |
| JP | 2010-530082 | A | 9/2010 |
| JP | 3171344 | U | 10/2011 |
| JP | 2011-249267 | A | 12/2011 |

* cited by examiner (a)

(b)

(a)

(b)

(a)

(b)

IMAGING APPARATUS AND METHOD FOR MANUFACTURING IMAGING APPARATUS

TECHNICAL FIELD

The present invention relates to an imaging device used for observing organisms, for example, and a method for manufacturing the imaging device.

BACKGROUND ART

Known as an example of techniques in this kind of field is an illumination device described in Patent Literature 1. In this conventional illumination device, flexible printed circuit boards constituting a plurality of segments are attached to the inside of a holding frame, so as to form a three-dimensional dome. Angles of surfaces on which light sources are placed in the respective boards are adjusted so that a specimen is irradiated with light in a desirable illuminance distribution.

Patent Literature 2 discloses an optical diagnostic system in which a plurality of excitation light emitting diodes are arranged in front of a camera such that their angles of illumination center axes with respect to the image pickup light axis differ from each other. Patent Literature 3 discloses an observation device in which a plurality of light sources are disposed within a hemispherical hood which is provided with an observation window on its upper part. This device forms the hood from an elastic material such as polyurethane. Patent Literature 4 discloses an illumination device in which LED arrays are arranged on a hemispherical substrate.

CITATION LIST

Patent Literature

Literature 1: Japanese Patent Application Laid-Open No. 2001-153808
Patent Literature 2: Japanese Patent Application Laid-Open No. 2008-183394
Patent Literature 3: Japanese Patent Application Laid-Open No. 2003-190103
Patent Literature 4: Japanese Patent Application Laid-Open No. H04-241476

SUMMARY OF INVENTION

Technical Problem

Devices such as those mentioned above are assumed not only to illuminate a subject to be imaged with light from a light source uniformly, but also to illuminate only a specific part thereof with the light, and to capture an image while changing the distance between the subject and imaging means. While this makes it necessary to adjust the optical axis of each light source in the device precisely, individually adjusting a plurality of light sources may complicate the working process or lower reproducibility. When an LED is used as a light source, for example, its output may become less stable when heat accumulates therein with use, whereby heat dissipation from the light source must be taken into consideration.

For solving the problems mentioned above, it is an object of the present invention to provide an imaging device which is easy to adjust the optical axis of a light source and excellent in heat dissipation of the light source, and a method for manufacturing such an imaging device.

Solution to Problem

For achieving the above-mentioned object, the imaging device in accordance with the present invention comprises a heat-dissipating base having an opening at a center; a flexible substrate, arranged on one surface side of the base, having an opening communicating with the opening of the base and an arrangement piece formed about the opening; a light source, arranged on one surface side of the arrangement piece, for emitting light toward a subject to be imaged; and imaging means, arranged coaxially with a center axis of the opening, for capturing at a deep part of the opening a light image from the subject; one surface side of the base is such a tilted surface as to form a depression having the opening as a bottom part; the arrangement piece is secured along the tilted surface so that an optical axis of the light source intersects the center axis of the opening.

In this imaging device, a tilted surface is formed on one surface side of a base, while a flexible substrate arranged with a light source is secured along the tilted surface of the base, so as to adjust the optical axis of imaging means and positions illuminated by the light source. Thus, respective optical axes of light sources are regulated not individually but at once by placing the substrate along the tilted surface, which makes it easy to adjust the illumination positions. It is also excellent in heat dissipation of the light source, since the heat generated by the light source dissipates through the base.

Preferably, the substrate has a plurality of arrangement pieces and a joint for joining the arrangement pieces at an edge of the opening. Joining the arrangement pieces with the joint makes it possible to use control circuits and the like of the light sources in common, thereby simplifying structures.

Preferably, the base has a plurality of tilted surfaces at respective angles different from each other. This makes it possible to set a plurality of positions illuminated with the light source with respect to the optical axis direction of the imaging means according to the number of angular patterns of the tilted surfaces.

Preferably, the tilted surfaces at different angles are arranged concentrically about the opening. This can easily form the tilted surfaces at different angles.

Preferably, the tilted surfaces at different angles are arranged circumferentially about the opening. This can easily form the tilted surfaces at different angles.

Preferably, the base and the substrate are secured to each other with a thermally conductive adhesive tape. This can secure heat conduction between the substrate and base, whereby heat can dissipate more efficiently from the light source.

Preferably, the imaging means comprises an image pickup element for capturing an image and a focus lens for adjusting a focus of the image pickup element, while the imaging device further comprises lens position detection means for detecting a position of the focus lens and light source switching means for turning on/off light sources arranged on the tilted surfaces at different angles according to a result of detection of the lens position detection means. This can switch between illumination positions of the light sources according to the focus of the image pickup element, thereby improving operability.

The method for manufacturing an imaging device in accordance with the present invention is a method for manufacturing an imaging device comprising a heat-dissipating base having an opening at a center; a flexible substrate, arranged on one surface side of the base, having an opening communicating with the opening of the base and an arrangement piece formed about the opening; a light source, arranged on one surface side of the arrangement piece, for emitting light toward a subject to be imaged; and imaging means, arranged coaxially with a center axis of the opening, for capturing at a deep part of the opening a light image from the subject; the method comprising forming one surface side of the base with such a tilted surface as to form a depression having the opening as a bottom part and securing the arrangement piece along the tilted surface so that an optical axis of the light source intersects the center axis of the opening.

This method for manufacturing the imaging device forms a tilted surface on one surface side of a base and secures a flexible substrate arranged with a light source along the tilted surface of the base, thereby adjusting the optical axis of the light source and positions illuminated by the light source. Respective optical axes of light sources are regulated not individually but at once by placing the substrate along the tilted surface, which makes it easy to adjust the illumination positions. It is also excellent in heat dissipation of the light source, since the heat generated by the light source can dissipate through the base.

Advantageous Effects of Invention

The imaging device and method for manufacturing an imaging device in accordance with the present invention is easy to adjust the optical axis of a light source and excellent in heat dissipation of the light source.

DESCRIPTION OF EMBODIMENTS

In the following, preferred embodiments of the imaging device and method for manufacturing an imaging device in accordance with the present invention will be explained in detail with reference to the drawings.

Figure 1:
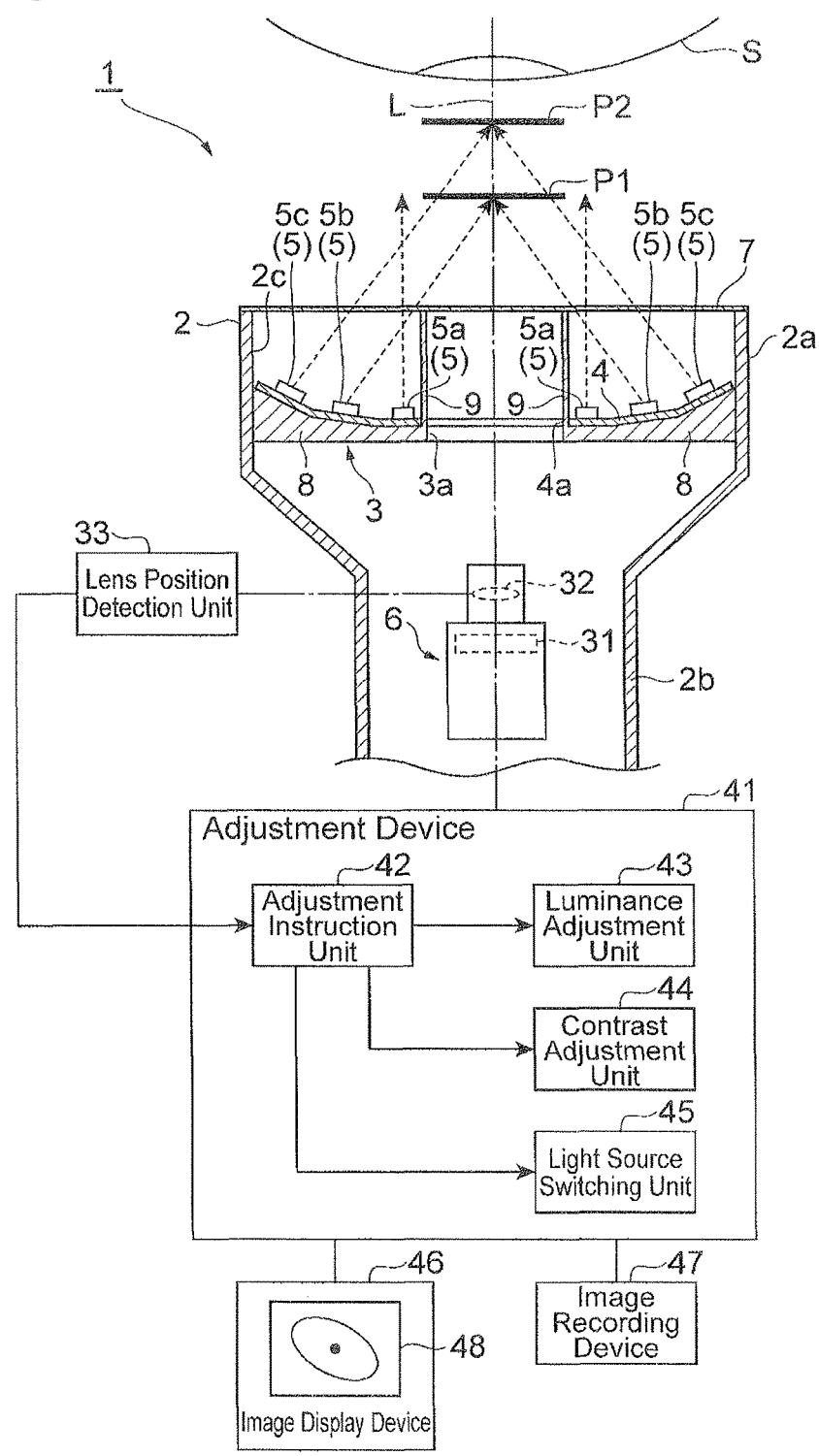
FIG. 1 is a diagram illustrating an embodiment of the imaging device in accordance with the present invention.

FIG. 1 is a diagram illustrating one embodiment of the imaging device in accordance with the present invention. As depicted, this imaging device 1 is constituted by a housing 2, a base 3, a substrate 4, light sources 5, and an imaging unit (imaging means) 6. The imaging device 1 is constructed as a device for irradiating a subject to be imaged S including lymph nodes, lymph vessels, blood vessels, cells, and the like existing under a tissue surface, for example, with excitation light having a predetermined wavelength and observing a fluorescent image emitted from the subject S in response thereto, thereby acquiring images under the tissue surface. For acquiring such images, for example, a dye such as a fluorescent dye, a photosensitizer, or a biomarker is injected into the subject S beforehand, so as to be accumulated in the lymph nodes and the like. Examples of dyes such as fluorescent dyes, photosensitizers, and biomarkers include indocyanine green, indocyanine blue, 5ALA, methylene blue, fluorescein, Laserphyrin, Photofrin, Patent Blue, indigo carmine, Qdot (registered trademark), and Genhance (registered trademark).

The housing 2 is formed into a substantially cylindrical shape by a member such as a metal excellent in heat dissipation, examples of which include aluminum, copper, magnesium, and iron. A leading end part 2a of the housing 2 has a diameter larger than that of a rear end part 2b and is provided with a circular opening 2c at its leading end. A transparent window member 7 is attached to the opening 2c so as to cover it.

Figure 2:
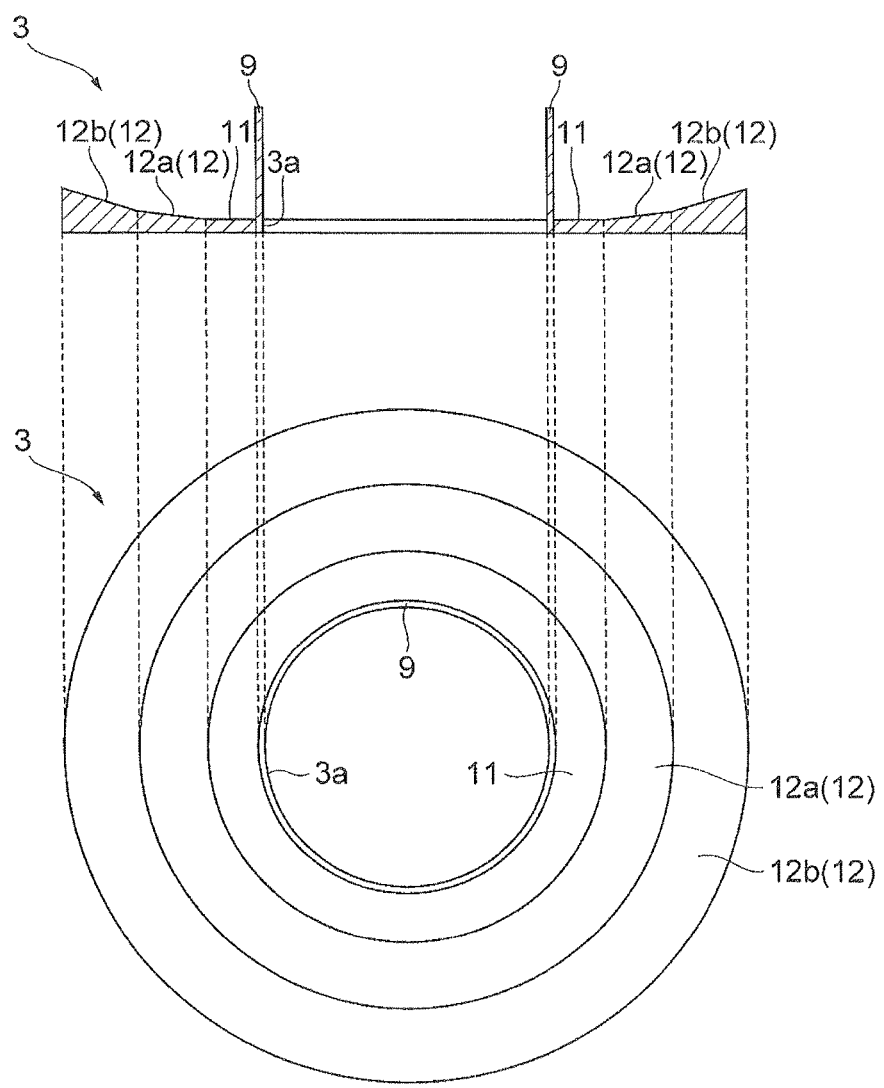
FIG. 2 is a diagram illustrating a base incorporated in the imaging device.

As illustrated in FIG. 2, the base 3 is formed by a member excellent in heat dissipation such as a metal. The base 3 has a substantially disk-shaped support 8 and a cylindrical light-shielding wall 9. A circular opening 3a for transmitting therethrough a fluorescent image from the subject S toward the imaging unit 6 is formed at the center of the base 3, while the light-shielding wall 9 is formed at an edge part of the opening 3a. Formed on one surface side of the support 8 are a planar part 11 arranged like a circular ring about the light-shielding wall 9 and a tilted surface 12 arranged concentrically with the planar part 11 on the outer peripheral side thereof. A connector (not depicted) for connecting a signal line for controlling the light sources 5 is formed at a given position of the planar part 11. The leading end of the light-shielding wall 9 is provided with a black flexible light-shielding member (not depicted) and is in contact with the window member 7 through the light-shielding member.

The tilted surface 12 comprises tilted surfaces 12a, 12b, which have respective angles different from each other, successively from the center side of the opening 3a, while the tilted surface 12b has an angle of inclination greater than that of the tilted surface 12a. The tilted surface 12b is located closer to the window member 7 than is the tilted surface 12a. This forms a depression having the opening 3a as a bottom part on one surface side of the base 3. An outer peripheral part of the base 3 is arranged within the leading end part 2a of the housing 2 and is firmly secured to the housing 2 by bonding with a thermally conductive adhesive such as those based on epoxy, for example, or a thermally conductive double-sided tape, by screwing, or the like. A thermally conductive grease may be applied between the base 3 and housing 2.

Figure 3:
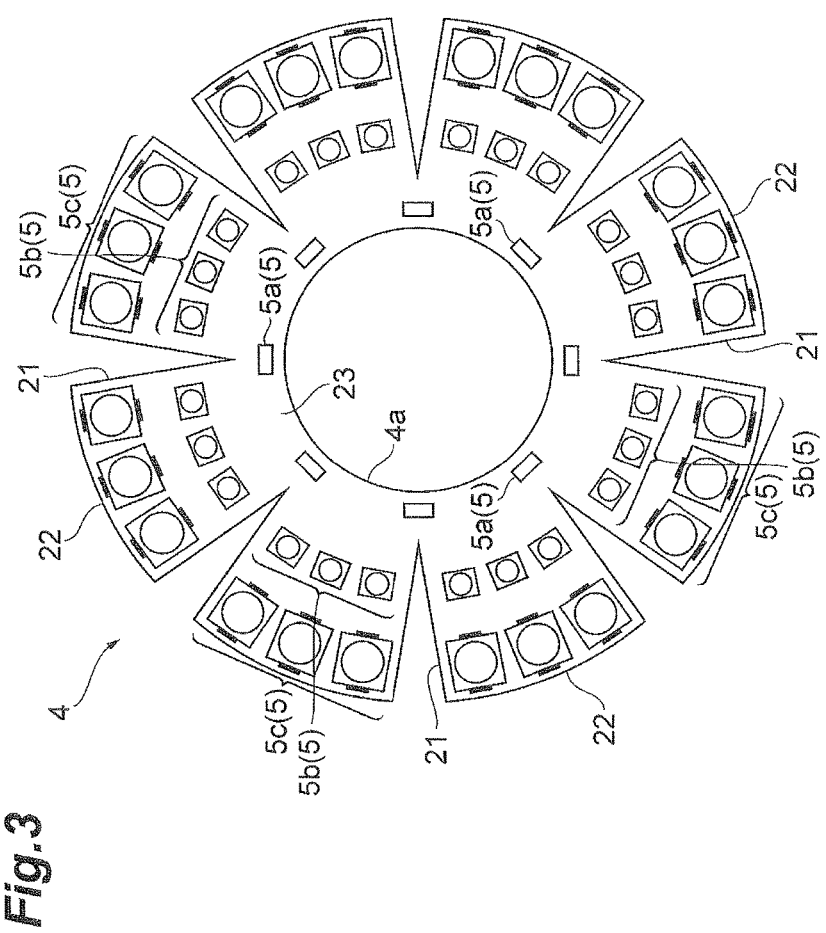
FIG. 3 is a diagram illustrating a substrate and a light source in an unfolded state.

The substrate 4 is a substrate having flexibility, examples of which include flexible substrates and membrane substrates. The substrate 4 is provided with circuit patterns for the light sources 5, lands for attaching the light sources 5, connector lands for external wiring, and the like as appropriate. As illustrated in FIG. 3, the substrate 4 is shaped into a substantially disk form having a diameter larger than that of the base 3. Formed at the center of the substrate 4 is an opening 4a having a diameter larger than that of the opening 3a of the base 3.

In this substrate 4, a plurality of incisions 21 are formed at predetermined angular intervals about the opening 4a. Each incision 21 has a substantially triangular form projecting toward the center of the opening 4a, while the distance from the leading end of the incision 21 to the edge of the opening 4a roughly equals the width of the planar part 11 of the base 3. Forming such incisions 21 produces a plurality of arrangement pieces 22 for arranging the light sources 5 between the incisions 21, 21 of the substrate 4. The arrangement pieces 22 are formed at predetermined intervals about the opening 4a. The incisions 21 fall short of reaching the opening 4a, whereby a joint 23 which joins the arrangement pieces 22 together is formed at the edge of the opening 4a. The incisions 21 are not limited to substantially triangular forms, but may be substantially oblong.

The light sources 5 are constructed so as to include white light sources 5a for color images, first excitation light sources 5b for short distances, and second excitation light sources 5c for long distances. The white light sources 5a, examples of which include white light-emitting diodes, are arranged between the leading end of the incision 21 and the opening 4a so as to form a ring in the joint 23 of the substrate 4.

For the first and second excitation light sources 5b, 5c, examples of which include light-emitting diodes (LED) and semiconductor lasers (LD), those having such a wavelength as to be able to excite fluorescent dyes injected into the subject S are selected. When the above-mentioned indocyanine green is used as a fluorescent dye, its light absorption band is in the infrared wavelength band, whereby a light source having a wavelength (e.g., 760 nm) in this wavelength band is used. The first excitation light sources 5b are surface-mounted by a plural number on the base end side of each arrangement piece 22, so as to be arranged like a ring about the opening 4a as a whole. The first and second excitation light sources 5b, 5c may be light sources on the same wavelength band or different wavelength bands.

Figure 4:
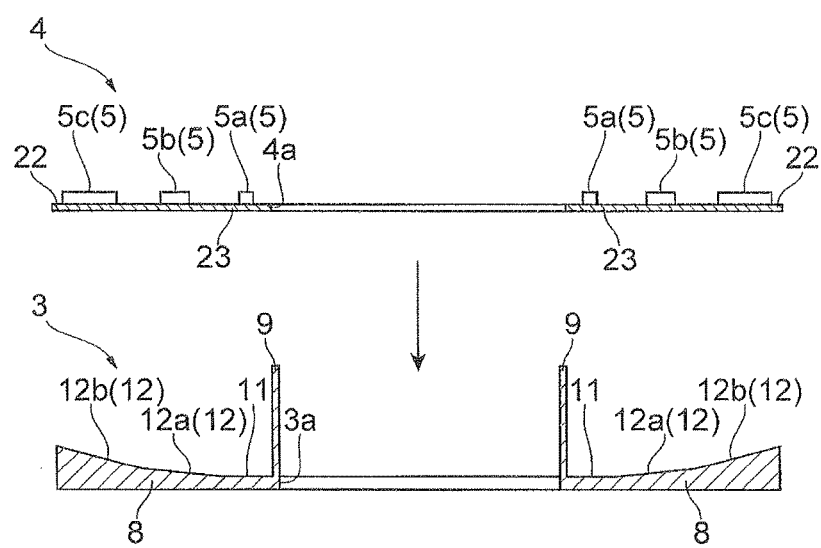
FIG. 4 is a diagram illustrating a process of manufacturing the imaging device illustrated in FIG. 1.
Figure 4:
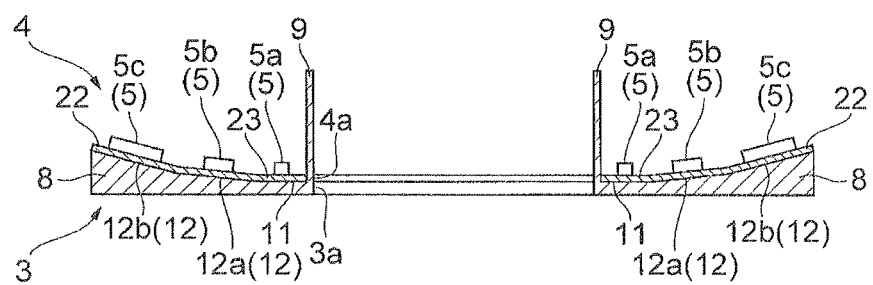

For attaching the substrate 4 to the base 3, the substrate 4 arranged with the light sources 5 and the base 3 are prepared separately as illustrated in FIG. 4(a). Then, with a heat-dissipating double-sided tape or a thermally conductive adhesive such as one based on epoxy, for example, the substrate 4 is brought into contact with and secured to the base 3 so as to extend along one surface side thereof while being positioned such that the openings 3a, 4a communicate with each other, the joint 23 coincides with the planar member 11, and the arrangement pieces 22 conform to the tilted surface 12. At this time, since the substrate 4 has flexibility and is provided with the incisions 21, as illustrated in FIG. 4(b), each arrangement piece 22 follows the planar part 11 in the vicinity of the first excitation light sources 5b, tilts in conformity to the angle of inclination of the tilted surface 12a in the vicinity of the first excitation light sources 5b, and tilts in conformity to the angle of inclination of the tilted surface 12b in the vicinity of the second excitation light sources 5c.

Each arrangement piece 22 tilts according to the inclinations of the tilted surfaces 12a, 12b, so that, as illustrated in FIG. 1, the optical axes of the first excitation light sources 5b intersect the center axis L of the opening 3a on the short distance side as seen from the imaging unit 6 so as to form a first illumination position P1, while the optical axes of the second excitation light sources 5c intersect the center axis L of the opening 3a on the long distance side as seen from the imaging unit 6 so as to form a second illumination position P2.

The imaging unit 6 is constructed so as to include an image pickup element 31 for capturing images and a focus lens 32 for adjusting a focus of the image pickup element 31 and arranged on the deep side of base 3 in the housing 2 such that its optical axis coincides with the center axis L of the opening 3a in the base 3. As the image pickup element 31, CCD sensors and CMOS sensors which can acquire two-dimensional images are used, for example. In this imaging device 1, elements having high sensitivity for the wavelength band of fluorescent images are used preferably.

The focus lens 32 is provided with drive means such as a lens mount, for example. Driving the focus lens 32 along the center axis L with this drive means can move the focus of the imaging unit 6. The position of the focus lens 32 with respect to the optical axis of the image pickup element 31 is detected by a lens position detection unit (lens position detection means) 33, and a signal including the result of detection is outputted to an adjustment device 41. Stepping motors and the like may be used as the drive means.

As illustrated in FIG. 1, the imaging device 1 is equipped with the adjustment device 41 for adjusting outputted observation images. The adjustment device 41 is a device which automatically or manually adjusts image data of observation images outputted from the imaging device 1. The adjustment device 41 has an adjustment instruction unit 42, a luminance adjustment unit 43, a contrast adjustment unit 44, and a light source switching unit (light source switching means) 45 as functional constituents.

The adjustment instruction unit 42 is a part which sets adjustment conditions for observation images automatically or in response to inputs from users. The adjustment instruction unit 42 instructs the luminance adjustment unit 43 and contrast adjustment unit 44 according to the set conditions, while the luminance adjustment unit 43 and contrast adjustment unit 44 adjust the luminance and contrast of the observation images, respectively.

The adjustment instruction unit 42 also receives the signal from the lens position detection unit 33 and determines whether the focus of the imaging unit 6 is located closer to the first illumination position P1 or the second illumination position P2. Then, the adjustment instruction unit 42 outputs to the light source switching unit 45 such an instruction signal as to turn on the light sources 5 forming the illumination position closer to the focus but turn off the light sources 5 forming the illumination position farther from the focus. According to the received instruction signal, the light source switching unit 45 turns on/off the first and second excitation light sources 5b, 5c arranged on the tilted surfaces 12a, 12b at respective angles different from each other.

When the adjustment conditions are fixed or no switch between ON and OFF of the light sources 5 is necessary, the adjustment instruction unit 42 may be omitted. The image data may be transferred from the imaging device 1 to the adjustment device 41 through a wire or wirelessly.

An image display device 46 and an image recording device 47 are connected to the adjustment device 41. The image display device 46 causes a display unit 48 to display the observation images adjusted by the adjustment device 41. A CRT monitor or a liquid crystal display attached to the imaging unit 6, for example, can be used as the image display device 46. The image recording device 47 is a device which records data of the observation images adjusted by the adjustment device 41. A video tape recorder, for example, can be used as the image recording device 47.

In the imaging device 1, as explained in the foregoing, the tilted surface 12 is formed on one surface side of the base 3, and the flexible substrate 4 arranged with the light sources 5 are secured along the tilted surface 12 of the base 3, so as to adjust the optical axis of the imaging unit 6 and positions illuminated by the light sources 5. Thus, the respective optical axes of the light sources 5 are regulated not individually but at once by placing the substrate along the tilted surface, which makes it easy to adjust the illumination positions. It is also excellent in heat dissipation of the light sources 5, since the heat generated by the light sources 5 dissipates through the base 3. This enables the light sources 5 to keep their output stability favorably.

Making the incisions 21 forms the substrate 4 with a plurality of arrangement pieces 22 and the joint 23 for joining the arrangement pieces 22 at an edge of the opening 4a. Joining the arrangement pieces 22 with the joint 23 makes it possible to use control circuits and the like for the light sources 5 in common, thereby simplifying the structure of the imaging device 1.

The base 3 is formed with a plurality of tilted surfaces 12a, 12b having respective angles different from each other, while the first and second excitation light sources 5b, 5c for short and long distances are arranged on the tilted surfaces 12a, 12b, respectively. Thus forming the tilted surface 12 makes it possible to set a plurality of positions illuminated by the light sources 5 with respect to the optical axis direction of the imaging unit 6 according to the number of angular patterns of the tilted surface 12. In this embodiment, the tilted surfaces 12a, 12b having different angles are arranged concentrically about the opening 3a, whereby the tilted surface having different angles can be formed easily.

In the imaging device 1, the base 3 and substrate 4 are secured to each other with a thermally conductive double-sided tape, while the outer peripheral part of the base 3 is secured to the housing 2 with a thermally conductive adhesive. This ensures heat conduction from the substrate 4 to the housing 2 through the base 3, whereby heat can dissipate from the light sources 5 more efficiently. The double-sided tape can bond the base 3 and substrate 4 to each other more uniformly (with less irregularities) than adhesives do.

The imaging unit 6 has the image pickup element 31 for capturing images and the focus lens 32 for adjusting the focus of the image pickup element 31, while the imaging device 1 comprises the lens position detection unit 33 for detecting the position of the focus lens 32 and the light source switching unit 45 for turning on/off the light sources 5 arranged on the tilted surfaces 12 at the respective angles different from each other. This makes it possible to switch between positions illuminated by the light sources 5 according to the focus of the image pickup element 31, whereby operability can be improved.

The base 3 is formed with the light-shielding wall 9, while a light-shielding member is interposed between the leading end of the light-shielding wall 9 and window member 7. This can prevent light emitted from the light sources 5 from being reflected by the window member 7 and made incident on the imaging unit 6. The planar part 11 is formed about the light-shielding wall 9, while the tilted surface 12 is formed on the outside of the planar part 11. This can inhibit light from the light sources 5 arranged on the tilted surface 12 from directly irradiating the light-shielding wall 9.

The tilted surface 12 has the tilted surfaces 12a, 12b at respective angles of inclination different from each other such that the tilted surface 12b located farther from the light-shielding wall 9 has an angle of inclination greater than that of the tilted surface 12a located closer to the light-shielding wall 9. This can further inhibit the light from the light sources 5 from directly irradiating the light-shielding wall 9.

In the imaging device 1, the first and second excitation light sources 5b, 5c for short and long distances are arranged on the tilted surfaces 12a, 12b farther from and closer to the window member 7, respectively. As a consequence, the distance from the first excitation light source 5b to the illumination position P1 is on a par with the distance from the second excitation light source 5c to the illumination position P2, whereby the illumination intensity at the illumination position P1 can be about the same as that at the illumination position P2. Without being restricted to this structure, however, the first and second excitation light sources 5b, 5c for short and long distances may be arranged on the tilted surfaces 12b, 12a closer to and farther from the window member 7, respectively.

In the imaging device 1, the tilted surface 12b is disposed on the outside of the tilted surface 12a concentrically therewith in the base 3, while the first and second excitation light sources 5b, 5c for short and long distances are arranged on the tilted surfaces 12a, 12b, respectively. Thus arranging a large number of the second excitation light sources 5c for long distances on the tilted surface 12 having a greater area can ensure the illumination intensity at the second illumination position P2.

Figure 5:
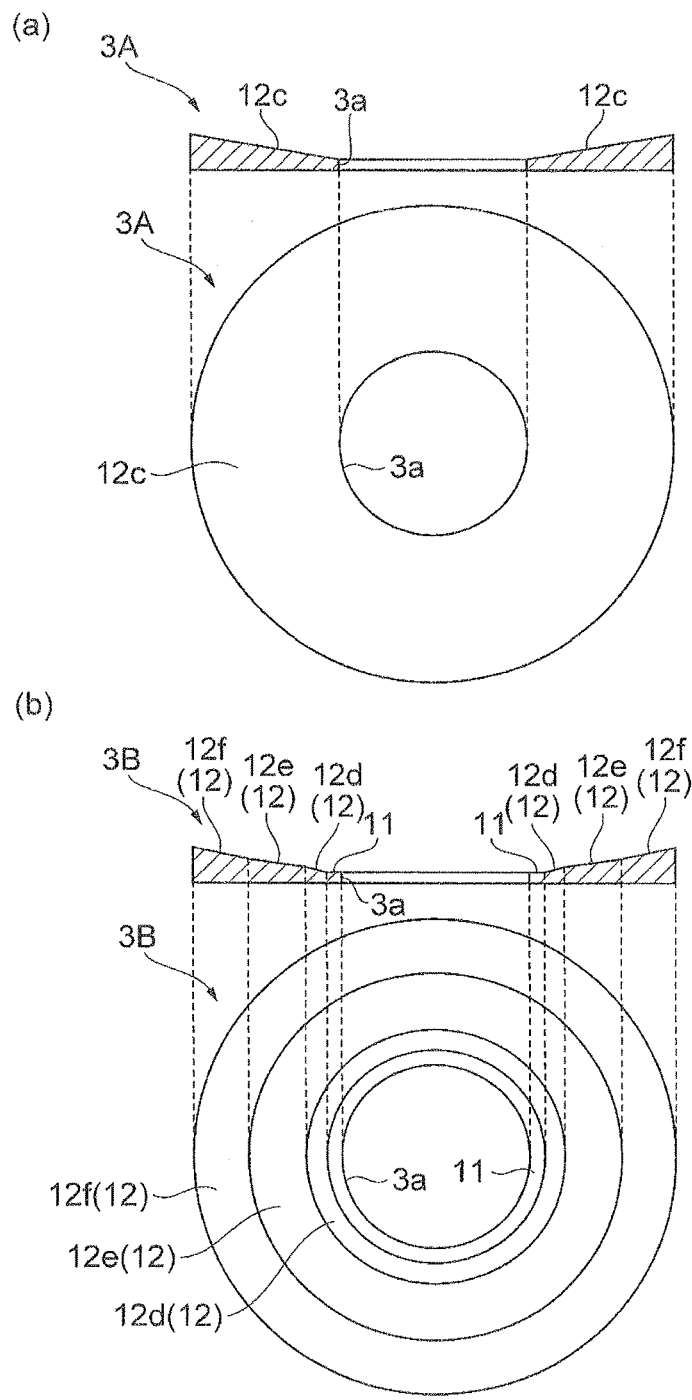
FIG. 5 is a diagram illustrating a modified example of the base.

The present invention is not limited to the above-mentioned embodiment. For example, while the planar part 11 and tilted surfaces 12a, 12b are disposed concentrically on one surface side of the base 3, angular patterns of the tilted surface 12 can be changed as appropriate according to specifications; a base 3A may be provided with one kind of tilted surface 12c alone as illustrated in FIG. 5(a); a base 3B may be provided with the planar member 11 and three kinds of tilted surfaces 12d, 12e, 12f concentrically as illustrated in FIG. 5(b).

Figure 6:
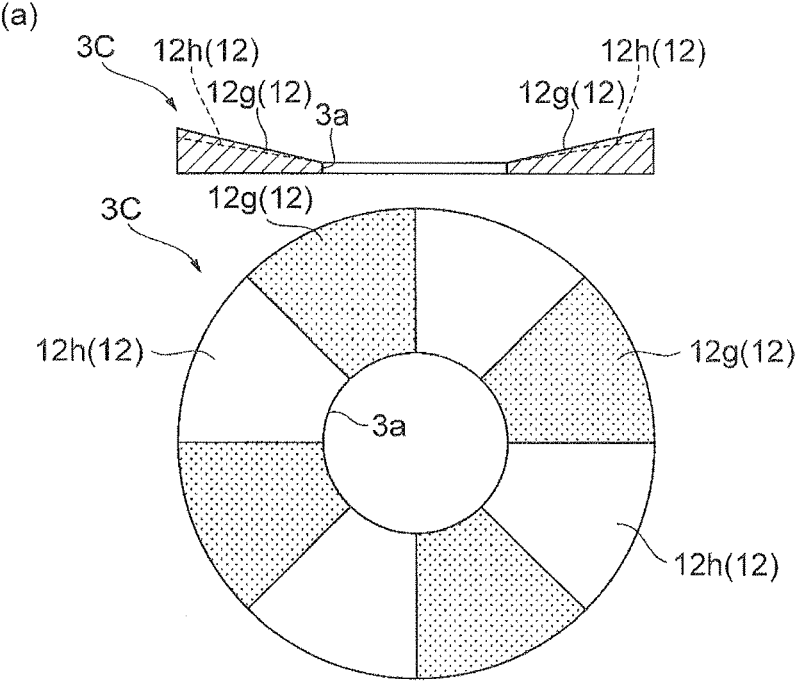
FIG. 6 is a diagram illustrating further modified examples of the base.
Figure 6:
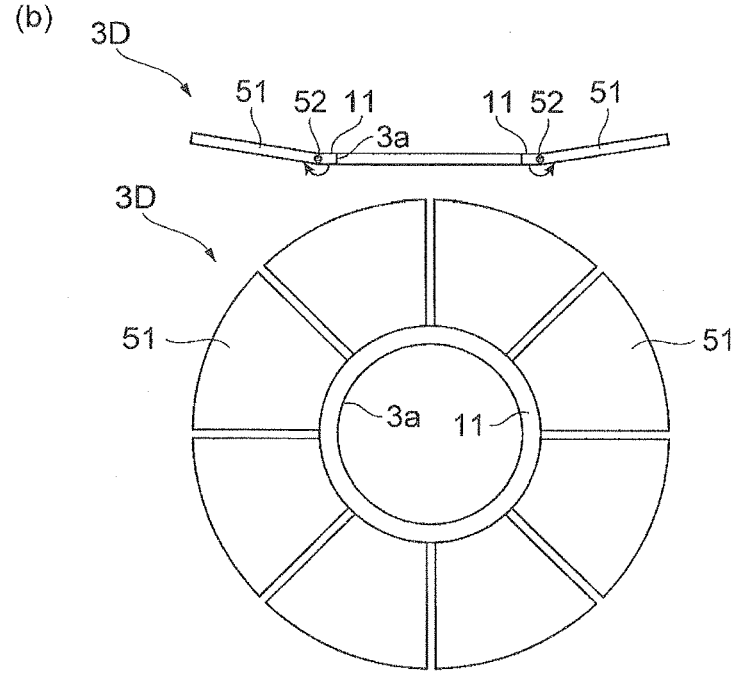

The arrangement pattern of the tilted surface 12 is not required to be concentric; a base 3C in which the tilted surface 12 is arranged circumferentially about the opening 3a as illustrated in FIG. 6(a) may be used. While two kinds of tilted surfaces 12g, 12h having respective angles different from each other are provided in an example illustrated in FIG. 6(a), angular patterns may further be increased, and a planar member similar to the planar member 11 may be disposed about the opening 3a.

As illustrated in FIG. 6(b), a base 3D may be formed into a flat disk, a plurality of incisions 21 may be formed with predetermined phase angles about the opening 3a so as to provide base pieces 51, and a hinge 52 may be attached to the base end part of each base piece 51 so that the latter can tilt at a given angle. Such a structure enables the angular adjustment of the base pieces 51 to regulate the angles of inclination of the arrangement pieces 22 of the substrate 4 secured to the base 3, whereby the positions illuminated by the light sources 5 can be adjusted freely. In each base piece 51, the part located closer to the center than is the hinge 52 may be the planar part 11.

Figure 7:
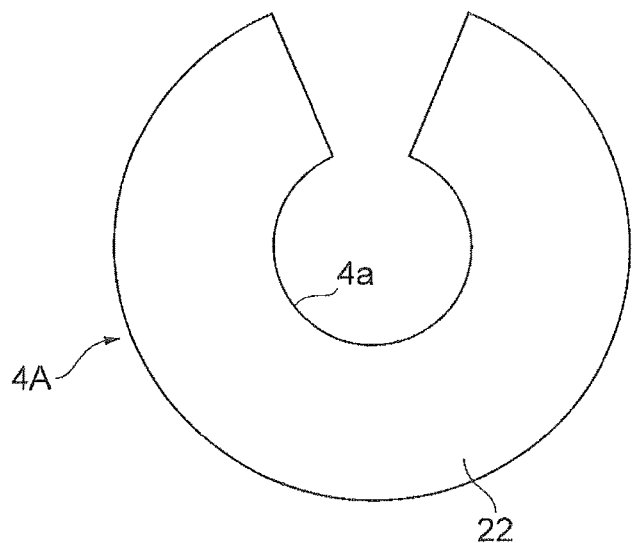
FIG. 7 is a diagram illustrating modified examples of the substrate.
Figure 7:
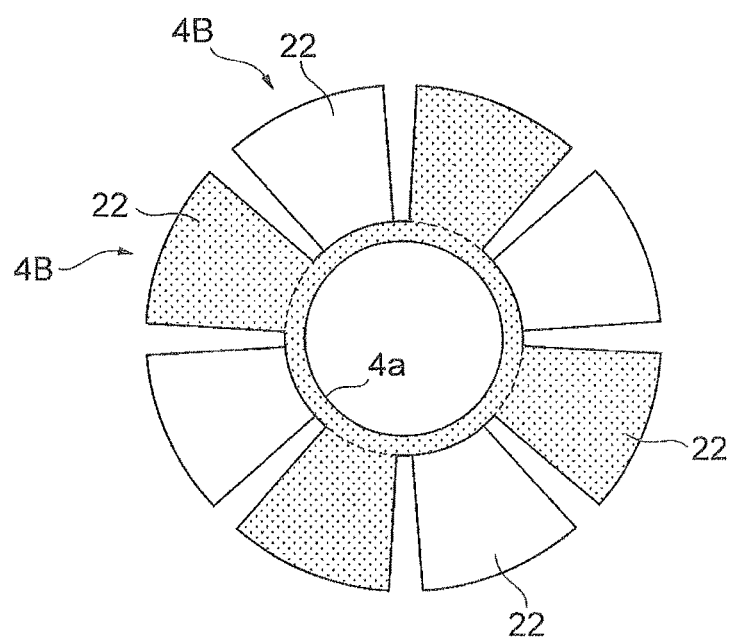

On the other hand, various deformations are applicable to the flexible substrate 4. For example, as illustrated in FIG. 7(a), a substrate 4A having one continuous arrangement piece 22 by forming an incision 21 at a given position so as to reach the opening 4a may be used, and a substrate having a two-dimensional form similar to that illustrated in FIG. 3 may be constructed as illustrated in FIG. 7(b) by superposing substrates 4B, 4B, each formed with a plurality of arrangement pieces 22 about the opening 4a, on each other.

Figure 8:
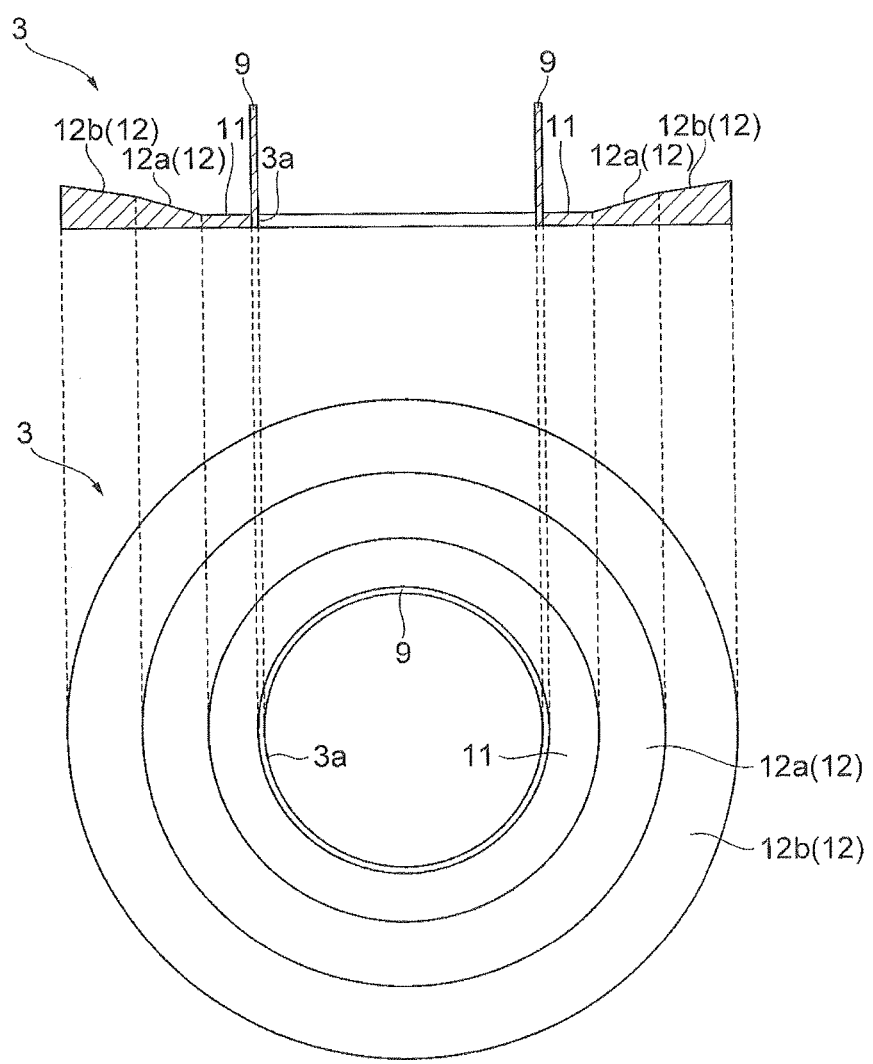
FIG. 8 is a diagram illustrating a modified example of a tilted surface of the base.

In the base 3, the angle of inclination of the tilted surface 12b on the outer periphery side may be greater than that of the tilted surface 12a on the opening 3a side as in the above-mentioned embodiment, or vice versa as illustrated in FIG. 8. In the latter case, arranging the first and second excitation light sources 5b, 5c for short and long distances on the tilted surfaces 12a, 12b having smaller and greater angles of inclination, respectively, makes it easier for light to irradiate both of the first and second irradiation positions P1, P2. However, the second and first excitation light sources 5c, 5b for long and short distances may be arranged on the tilted surfaces 12a, 12b, respectively.

While this embodiment illustrates an imaging device for observing fluorescence, the imaging device in accordance with the present invention is not limited to those for observing fluorescence, but is also employable for other uses, example of which include observing emitted light, absorbed light, and reflected light.

REFERENCE SIGNS LIST

1: imaging device; 3, 3A to 3D: base; 3a: opening; 4, 4A, 4B: substrate; 4a: opening; 5 (5a to 5c): light source; 6: imaging unit (imaging means); 12 (12a to 12h): tilted surface; 22: arrangement piece; 23: joint; 31: image pickup element; 32: focus lens; 33: lens position detection unit (lens position detection means); L: center axis; S: subject to be imaged.

The invention claimed is:

1. An imaging device comprising:
a heat-dissipating base having an opening at a center;
a flexible substrate, arranged on one surface side of the base, the one surface side of the base being a tilted surface that forms a depression having the opening as a bottom part, the flexible substrate comprising:
an opening communicating with the opening of the base; and
a plurality of arrangement pieces disposed in concentric rows about the opening of the base;
a plurality of light sources for emitting light toward a subject to be imaged, one of the plurality of arrangement pieces being disposed between each of the plurality of light sources and the tilted surface of the one surface side of the base, each of the plurality of light sources having an optical axis that intersects a center axis of the opening of the base; and
an image sensor, arranged coaxially with the center axis of the opening of the base, for capturing at a deep part of the opening of the base a light image from the subject.

2. The imaging device according to claim 1, wherein the base has a plurality of tilted surfaces at respective angles different from each other.

3. The imaging device according to claim 2, wherein the tilted surfaces at different angles are arranged concentrically about the opening.

4. The imaging device according to claim 2, wherein the tilted surfaces at different angles are arranged circumferentially about the opening.

5. The imaging device according to claim 1, wherein the base and the substrate are secured to each other with a thermally conductive adhesive tape.

6. The imaging device according to claim 1, wherein the image sensor comprises an image pickup element for capturing an image and a focus lens for adjusting a focus of the image pickup element; wherein the imaging device receives a position of the focus lens; and
wherein the plurality of light sources are arranged on the tilted surfaces at different angles according to a result of detection of the position of the focus lens.

7. A method for manufacturing an imaging device comprising:
a heat-dissipating base having an opening at a center;
a flexible substrate, arranged on one surface side of the base, the one surface side of the base being a tilted surface that forms a depression having the opening as a bottom part, the flexible substrate comprising:
an opening communicating with the opening of the base; and
a plurality of arrangement pieces disposed in concentric rows about the opening of the base;
a plurality of light sources for emitting light toward a subject to be imaged, one of the plurality of arrangement pieces being disposed between each of the plurality of light sources and the tilted surface of the one surface side of the base, each of the plurality of light sources having an optical axis that intersects a center axis of the opening of the base; and
an image sensor, arranged coaxially with the center axis of the opening of the base, for capturing at a deep part of the opening of the base a light image from the subject;
the method comprising:
forming the one surface side of the base being tilted surface that forms a depression having the opening as a bottom part; and
securing the plurality of arrangement pieces along the tilted surface so that an optical axis of each of the plurality of light sources intersects the center axis of the opening of the base.

8. The imaging device according to claim 1, wherein the flexible substrate has a plurality of incisions formed at predetermined angular intervals about the opening.

9. The imaging device according to claim 8, wherein at least some of the plurality of arrangement pieces are distributed along portions of the substrate between two of the plurality of incisions.

10. The method for manufacturing an imaging device according to claim 7, further comprising forming a plurality of incisions at predetermined angular intervals about the opening in the flexible substrate.

11. The method for manufacturing an imaging device according to claim 10, wherein at least some of the plurality of arrangement pieces are distributed along portions of the substrate between two of the plurality of incisions.

* * * * *